US012257385B2

(12) United States Patent
Graber et al.

(10) Patent No.: US 12,257,385 B2
(45) Date of Patent: Mar. 25, 2025

(54) LIQUID VENTILATION SYSTEM

(71) Applicant: Alcor Life Extension Foundation, Inc., Scottsdale, AZ (US)

(72) Inventors: Steven Daniel Graber, Scottsdale, AZ (US); Jacob Daniel Graber, Scottsdale, AZ (US)

(73) Assignee: Alcor Life Extension Foundation, Inc.

( * ) Notice: Subject to any disclaimer, the term of this patent is extended or adjusted under 35 U.S.C. 154(b) by 838 days.

(21) Appl. No.: 17/449,441

(22) Filed: Sep. 29, 2021

(65) Prior Publication Data

US 2023/0099428 A1    Mar. 30, 2023

(51) Int. Cl.
*A61M 16/00* (2006.01)
*A61M 16/04* (2006.01)

(52) U.S. Cl.
CPC .... *A61M 16/0054* (2013.01); *A61M 16/0003* (2014.02); *A61M 16/0057* (2013.01); *A61M 16/04* (2013.01); *A61M 2205/3368* (2013.01); *A61M 2230/432* (2013.01); *A61M 2230/435* (2013.01)

(58) Field of Classification Search
CPC .......... A61M 16/0054; A61M 16/0003; A61M 16/0057; A61M 2016/0027; A61M 16/04; A61M 2205/3368; A61M 2230/432; A61M 2230/435

See application file for complete search history.

(56) References Cited

U.S. PATENT DOCUMENTS

| 5,706,830 | A | * | 1/1998 | Parker | A61M 16/0404 |
| | | | | | 128/207.14 |
| 6,149,624 | A | * | 11/2000 | McShane | A61M 3/0258 |
| | | | | | 604/113 |
| 8,465,535 | B2 | | 6/2013 | Harris et al. | |
| 9,238,115 | B2 | * | 1/2016 | Homuth | A61M 16/12 |
| 10,046,126 | B2 | * | 8/2018 | Coleman | A61M 16/201 |
| 2010/0319691 | A1 | * | 12/2010 | Lurie | A61M 16/06 |
| | | | | | 128/205.24 |
| 2016/0271348 | A1 | * | 9/2016 | Nadeau | A61M 16/0054 |
| 2021/0077759 | A1 | * | 3/2021 | Micheau | A61F 7/0085 |
| 2021/0106746 | A1 | * | 4/2021 | Nightengale | A61M 1/3653 |

* cited by examiner

*Primary Examiner* — Samchuan C Yao
*Assistant Examiner* — Melis T. Jensen
(74) *Attorney, Agent, or Firm* — Thomas W. Galvani, P.C.; Thomas W. Galvani

(57) ABSTRACT

A liquid ventilation system includes a reservoir holding a perfluorochemical ("PFC") fluid, and a suction pump connected to the reservoir to reduce pressure within the reservoir. A sensor is configured to measure an intra-lung pressure. An appliance is configured to be disposed within a patient. The appliance carries an injector to supply the PFC fluid through the appliance. An extraction valve is disposed on an extraction line between the appliance and the reservoir. The extraction valve is arrangeable between a first position enabling fluid communication from the appliance to the reservoir and a second position disabling fluid communication from the appliance to the reservoir.

12 Claims, 3 Drawing Sheets

LIQUID VENTILATION SYSTEM

FIELD

The present specification relates generally to medical systems, and more particularly to medical ventilation systems.

BACKGROUND

A patient must usually receive medical attention immediately after a severe injury or traumatic event. Unfortunately, this is not always possible. For example, soldiers who are injured in remote locations may have to be carried a great distance or be evacuated by a helicopter. They may only receive basic first aid until they can make it back to a hospital. Such incidents require a faster way to get medical attention or a method for prolonging the time required to receive such attention.

Therapeutic hypothermia is one method of extending the window in which a patient should receive medical care. Therapeutic hypothermia lowers the body temperature five to ten degrees Celsius, which can provide an additional hour to the care window. Currently, there are two ways to cool the body: external chilling and internal chilling.

External chilling involves cooling the body from the outside only. Cooling pads and blankets, ice packs, and ice packs will lower body temperature non-invasively and in a relatively well-controlled manner. However, external chilling is slow, requires a great deal of gear, and is fairly modest in its ability to cool.

Internal chilling is cooling the body from within. Health workers sometimes apply chilled fluids through an IV line to chill a patient. This can be an effective method to chill the body. In the past thirty years, researchers have developed liquid ventilation ("LV") techniques. LV is the administration of perfluorochemicals ("PFC" or "PFCs") directly to the lungs. PFCs supply the lungs and heart with adequate supplies of oxygen. PFCs can be chilled significantly, and when applied to the body in a chilled state, they rapidly decrease body temperature.

Conventional LV system use a tidal volume application of PFCs, in which a bolus of PFCs is supplied to the lungs. Simultaneously, for patients with no pulse, a chest compression device ("thumper") compresses the chest to pump the heart and maintain blood circulation.

One drawback with these conventional systems is that the chest compression device operates cyclically, but application of the PFC is done in large impulses uncoordinated with that cycle. Chest compressions ("CPS") apply a tremendous amount of force to the lungs. PFCs are an incompressible fluid, and so the performance of chest compressions on lungs filled with PFCs can be traumatic. The deeper the lungs are infused with PFCs, the greater the possibility that they will be over-pressurized during a compression and thus damaged.

Conventional LV systems pre-measure a bolus of PFCs and essentially force-infuse the entire bolus into the lungs. The cyclic force of the thumper piston, however, will prevent PFCs from exiting the lungs fast enough; a fully-infused bolus of PFC in the lungs during a compression will over-pressurize and damage the lungs and can kill the patient. As such, liquid ventilation with conventional LC systems is inappropriate during life-saving CPS when the patient has lost a heartbeat. Conventional LV systems thus do not extend the care window in these instances.

Another drawback of conventional LV systems is their open configuration. A reservoir tank holding PFCs is open to the atmosphere, which prevents the development of back pressure when PFCs are pumped out of the reservoir. However, opening such systems exposes them to unknown contaminants which can then be administered inside a patient, to unknown and potentially harmful effect.

Conventional LV systems also use mechanical pumps to pull PFC fluid directly out of the lungs. However, the extraction rate is limited by the pump's performance characteristics. Faster extraction rates can be achieved but are typically provided only by large pumps which are heavy, bulky, consume a great deal of power, and produce considerable heat.

There is a need for PFC application to the lungs without the risks of over-pressurization.

SUMMARY

A liquid ventilation system includes a reservoir holding a perfluorochemical ("PFC") fluid, and a suction pump connected to the reservoir to reduce pressure within the reservoir. A sensor is configured to measure an intra-lung pressure. An appliance is configured to be disposed within a patient. The appliance carries an injector to supply the PFC fluid through the appliance. An extraction valve is disposed on an extraction line between the appliance and the reservoir. The extraction valve is arrangeable between a first position enabling fluid communication from the appliance to the reservoir and a second position disabling fluid communication from the appliance to the reservoir.

The above provides the reader with a very brief summary of some embodiments described below. Simplifications and omissions are made, and the summary is not intended to limit or define in any way the disclosure. Rather, this brief summary merely introduces the reader to some aspects of some embodiments in preparation for the detailed description that follows.

BRIEF DESCRIPTION OF THE DRAWINGS

Referring to the drawings.

DETAILED DESCRIPTION

Figure 1:
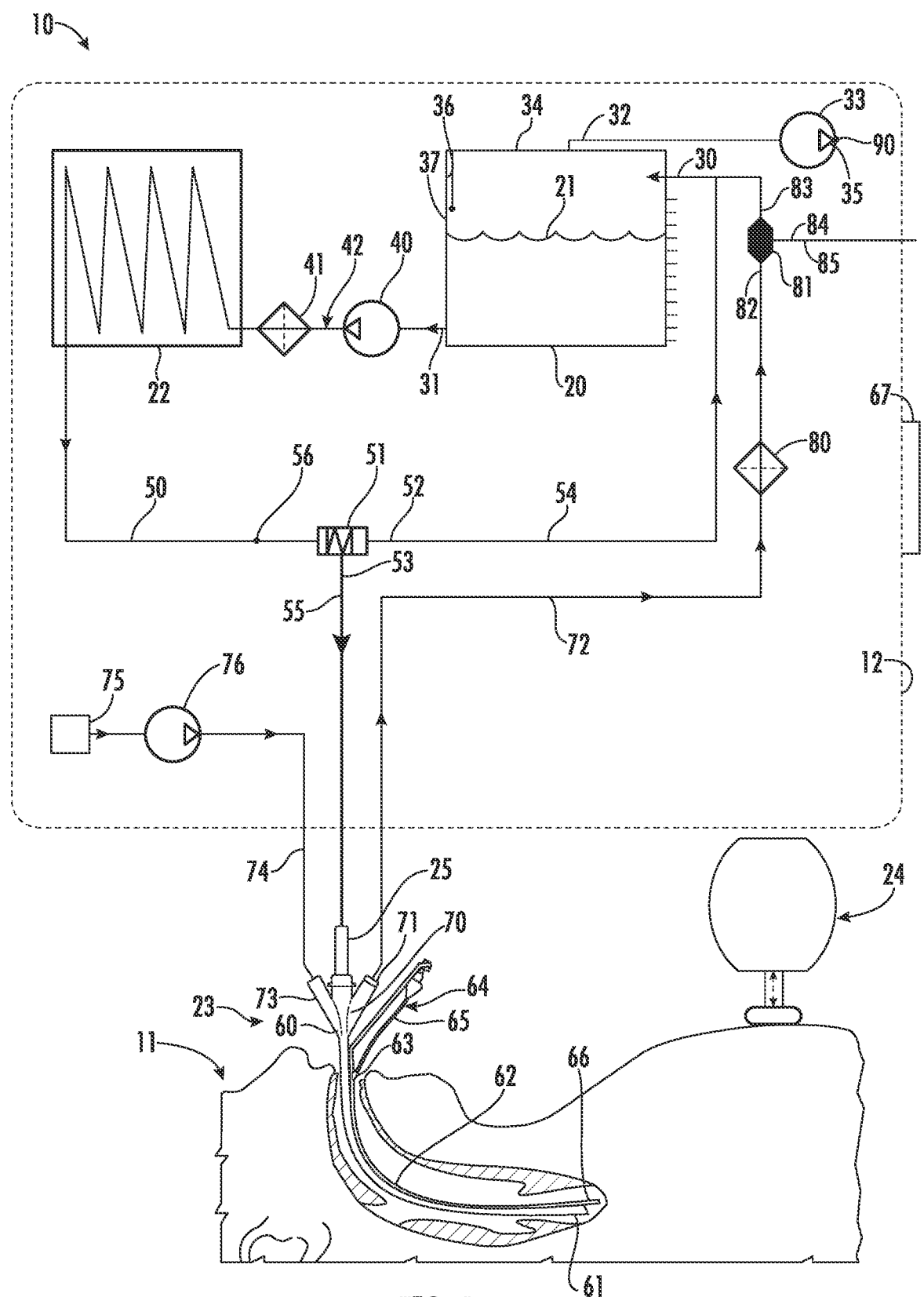
FIG. 1 is a schematic of a liquid ventilation system as applied to a human patient.

Reference now is made to the drawings, in which the same reference characters are used throughout the different figures to designate the same elements. Briefly, the embodiments presented herein are preferred exemplary embodiments and are not intended to limit the scope, applicability, or configuration of all possible embodiments, but rather to provide an enabling description for all possible embodiments within the scope and spirit of the specification. Description of these preferred embodiments is generally made with the use of verbs such as "is" and "are" rather than "may," "could," "includes," "comprises," and the like, because the description is made with reference to the drawings presented. One having ordinary skill in the art will understand that changes may be made in the structure, arrangement, number, and function of elements and features without departing from the scope and spirit of the specification. Further, the description may omit certain information which is readily known to one having ordinary skill in the art to prevent crowding the description with detail which is not necessary for enablement. Indeed, the diction used herein is meant to be readable and informational rather than to delineate and limit the specification; therefore, the scope and spirit of the specification should not be limited by the following description and its language choices.

FIG. 1 is a schematic illustration of a liquid ventilation system 10 for use with a patient 11. A housing 12 contains the system 10; the housing 12 is shown in FIG. 1 as a broken line of generic shape. In embodiments of the system 10, the housing 12 is a framework in or on which the constituent structural elements and features of the system 10 are mounted, while in other embodiments of the system 10, the housing 12 is a hard- or soft-shelled backpack, such that the system 10 can be carried into terrain for remote operation of the system 10. In a backpack embodiment of the housing 12, the constituent structural elements and features of the system 10 are packed tightly together to conserve space. For these reasons, FIG. 1 shows the housing 12 without a specific shape and without a specific arrangement of elements and features, and the reader will understand that the shape and arrangements shown in FIG. 1 are not limiting.

The system 10 includes a tank 20 to hold fluid 21, a chiller 22 to cool the fluid 21 before administration to the patient 11, and an appliance 23 to administer the fluid 21 to the patient 11. The system 10 is closed-loop; fluid 21 moves downstream from the tank 20, through the chiller 22, to the patient 11, and then back to the tank 20 without exposure to the outside environment. The system 10 works both with and without a chest compression machine 24 (or "thumper 24"). A fine-precision injector 25 carried at the mouthpiece precisely controls the very quickly- and discretely-metered administration of fluid 21 to the patient 11. Feedback from sensors placed within the patient 11 provide information useful for controlling the operation of the injector 25 to prevent harm to the patient 11. These elements, as well as those described below, enable the system 10 to lower the temperature of the patient 11 rapidly without risk of damage to the lungs or other body parts of the body of the patient 11.

The tank 20 is a rigid shell vessel. It acts as a reservoir to store a supply of PFC fluid 21 in liquid form. Briefly, the PFC fluid 21 described herein is a preferred fluid for use in the system 10, but the system 10 is suitable for use with other fluids, including both liquids and gasses. The term "fluid" is thus used herein to refer to PFC fluids as well as other liquids and gasses. The tank 20 optionally includes baffles to reduce sloshing and aeration of the PFC, and to allow visual measurement and observation, especially in embodiments with a view panel on the tank 20. The tank 20 includes an inlet 30, where fluid 21 is returned to the tank 20, and an outlet 31, where fluid 21 leaves the tank 20. Another port 32 is formed in the wall of the tank 20; the port 32 is coupled, via a line, pipe, hose, or the like, to a suction pump 33. Briefly, and unless otherwise specifically noted, the term "line" is used herein to refer to a fluid connection between two structural elements, such as the port 32 and the suction pump 33. The term line is non-limiting and is meant to include, at least, a tube, pipe, hose, or like structure sufficiently rigid and flexible and otherwise suitable for communication of a fluid, regardless of the internal geometry of such structure. The suction pump 33 runs continuously during operation of the system 10 to establish a vacuum or near vacuum, which is considered to be between approximately twelve PSI and three PSI absolute, but may in other embodiments be different. This operates to energetically extract fluid 21 out of the patient 11 and to draw off gas bubbles introduced to the tank 20 in fluid 21 returning through the inlet 30. The suction pump 33 has a safety cutoff switch to halt its operation at three PSI absolute. This value may be different in other embodiments. Preferably, the tank 20 has a redundant vacuum relief valve, such as a spring-loaded negative pressure valve, to prevent over suction on the lungs.

The suction pump 33 preferably is mounted at a "top" 34 of the tank 20 to enable this the drawing off of gas bubbles described in the above paragraph. In some embodiments of the system 10, the tank 20 is mounted with a particular orientation within the housing 12 so as to direct a portion—a top 34—of the tank 20 upwardly. In such embodiments, the suction pump 33 is located at the top 34 of the tank 20. When the tank 20 contains fluid 21, the top 34 of the tank 20 is likely to not be below the fluid 21, and so gasses which are less dense than the fluid 21 will rise to above the fluid 21 and become available to be drawn off by the suction pump 33. The suction pump 33 has an outlet 35 to the environment which exhausts gas from the suction pump 33.

The outlet 31 is mounted in a location roughly opposite the top 34 of the tank 20, such that the outlet 31 is near the bottom of the tank 20. A line is connected to the outlet 31 and extends downstream to a main pump 40. The main pump 40 pulls fluid 21 out of the tank 20 and moves it downstream. The main pump 40 is a high-pressure pump and, in some embodiments, is a variable-speed pump. The main pump 40 preferably operates continuously. Another line connects the main pump 40 to a filter 41, which separates particles, contaminants, and other elements from the fluid 21. Another line connects the filter 41 to the chiller 22 to further move fluid 21 downstream. The lines connecting the tank 20, the main pump 40, the filter 41, and the chiller 22 constitute and are collectively referred to herein as a supply line 42. The main pump 40 and filter 41 are in-line on that supply line 42. In the embodiment shown in FIG. 1, the filter 41 is downstream from the main pump 40 on the supply line 42; in other embodiments, that disposition is reversed.

The supply line 42 couples to the chiller 22 to pass fluid 21 thereto. The chiller 22 is a heat exchanger of any suitable type. Preferably, the chiller 22 is a compact heat exchanger. The chiller 22 cools the fluid 21 to just above the freezing temperature of water, around one to five degrees Celsius.

A thermocouple 56 is downstream from the chiller 22 and is connected to a computer 67, such as a tablet, desktop computer, server, Raspberry Pi or like device, logic controller, or other programmable controller, connecting the two in data communication. This thermocouple 56 measures the temperature of the fluid 21 exiting the chiller 22. The computer 67 receives and processes that measurement. Because the system 10 is relatively small, the lines within the system 10 are relatively short, and the system 10 is relatively compact and contained by the housing 12, there is relatively little increase in temperature of the fluid 21 from the chiller 22 to the patient 11. Moreover, in some embodiments, the lines are insulated. Nevertheless, fluid 21 returning from the patient 11 to the tank 20 is warmer and should be cooled before re-administration.

A line, referred to herein as a chilled line 50, extends from an outlet of the chiller 22 to a pressure regulator 51. The pressure regulator 51 is a three-way valve with a single inlet and two outlets: a recirculation outlet 52 and an administration outlet 53. The chilled line 50 is coupled to the inlet of the pressure regulator 51. A recirculation line 54 is coupled to the recirculation outlet 52 and extends back to the tank 20. An administration line 55 is coupled to the administration outlet 53 of the pressure regulator 51 and extends to the appliance 23. The pressure regulator 51 regulates the fluid pressure of the fluid 21 before it is supplied to the injector 25 in the appliance 23. The pressure regulator 51 is coupled to the computer 67 in data communication, both providing information to and receiving control signals from the computer 67.

In some embodiments of the system 10, the pressure regulator 51 is incorporated directly into the appliance 23, eliminating the administration line 55. In those embodiments, the lines 50, 54, and 72 are all coupled directly to the appliance 23. Thus configured, PFC fluid 21 is recirculated on a path from the chilled line 50, to the appliance 23, and back to the tank 20 via the recirculation line 54. The pressure regulator 51 is computer controlled in some embodiments and in other embodiments has an adjustable spring-based pressure relief mechanism that bypasses excess fluid 21 back to the tank 20 via the recirculation line 54. In other embodiments, the pressure regulator 51 may be set to a specific, fixed pressure limit for the fluid 21 that is delivered to the injector 25 via the administration line 55.

The recirculation line 54 extends back to the tank 20 where it couples to the inlet 30 of the tank 20. Typically, when the system 10 is energized, the pressure regulator 51 opens the recirculation outlet 52 and closes the administration outlet 53. During this initial stage of operation, and in this arrangement of the pressure regulator 51, the main pump 40 pumps fluid 21 out of the tank 20, through the chiller 22, through the pressure regulator 51 and then back to the tank 20, thereby recirculating the fluid 21 entirely within the housing 12. This keeps the fluid 21 cool and ready for administration to the patient 11. A thermocouple 36 within the tank 20 measures the temperature of the fluid 21 within the tank 20. The thermocouple 36 is coupled to the computer 67 in data communication. Additionally, there is a pressure transducer 37 within the tank 20 monitoring the vacuum conditions within the tank 20; the transducer 37 is also coupled to the computer 67 in data communication.

The administration line 55 extends outside of the housing 12 and is coupled to the appliance 23. When the patient 10 is prepared and the system 10 is readied, the pressure regulator 51 is arranged so that the recirculation outlet 52 closes and the administration outlet 53 opens. The main pump 40 then pumps fluid 21 out of the tank 20, through the chiller 22, through the pressure regulator 51 and then out of the housing 12 to the appliance 23, which is applied to the patient 10.

The appliance 23 is an endotracheal tube. It includes an upstream end 60 and an opposed downstream end 61. The upstream end 60 has several ports or fittings, and remains outside the body of the patient 11, while the downstream end is placed within the patient 11, as deep as the lower trachea, bronchial tube, or primary bronchus. The appliance 23 includes a cannula 62 extending between the upstream and downstream ends 60 and 61. The cannula 62 is an open tube configured to receive instruments and other elements therein, so that they may be easily applied to or beyond the open downstream end 61 of the appliance 23.

An opening 63 is formed in the cannula 62 proximate the upstream end 60 of the appliance 23. A sensor 64, supported on an arm outside the appliance 23, is threaded through the opening 63 and within the cannula 62. The opening 63 is sealed around the sensor 64. The sensor 64 is a pressure sensor and includes a long electrical lead 65 and a small pressure and temperature sensor, such as a transducer 66, at the end of that lead. The transducer 66 is preferably located just beyond the downstream end 61 of the appliance 23, so that it is disposed to measure an intra-lung pressure and temperature local to the transducer 66. In some embodiments, a secondary or redundant sensor is carried in the appliance 23 as a backup. The electrical lead 65 extends up from the transducer 66, though the opening 63 and onto the arm. A coupling then extends from the lead 65 to the computer 67, connecting the transducer 66 to the computer 67 in data communication.

Figure 2:
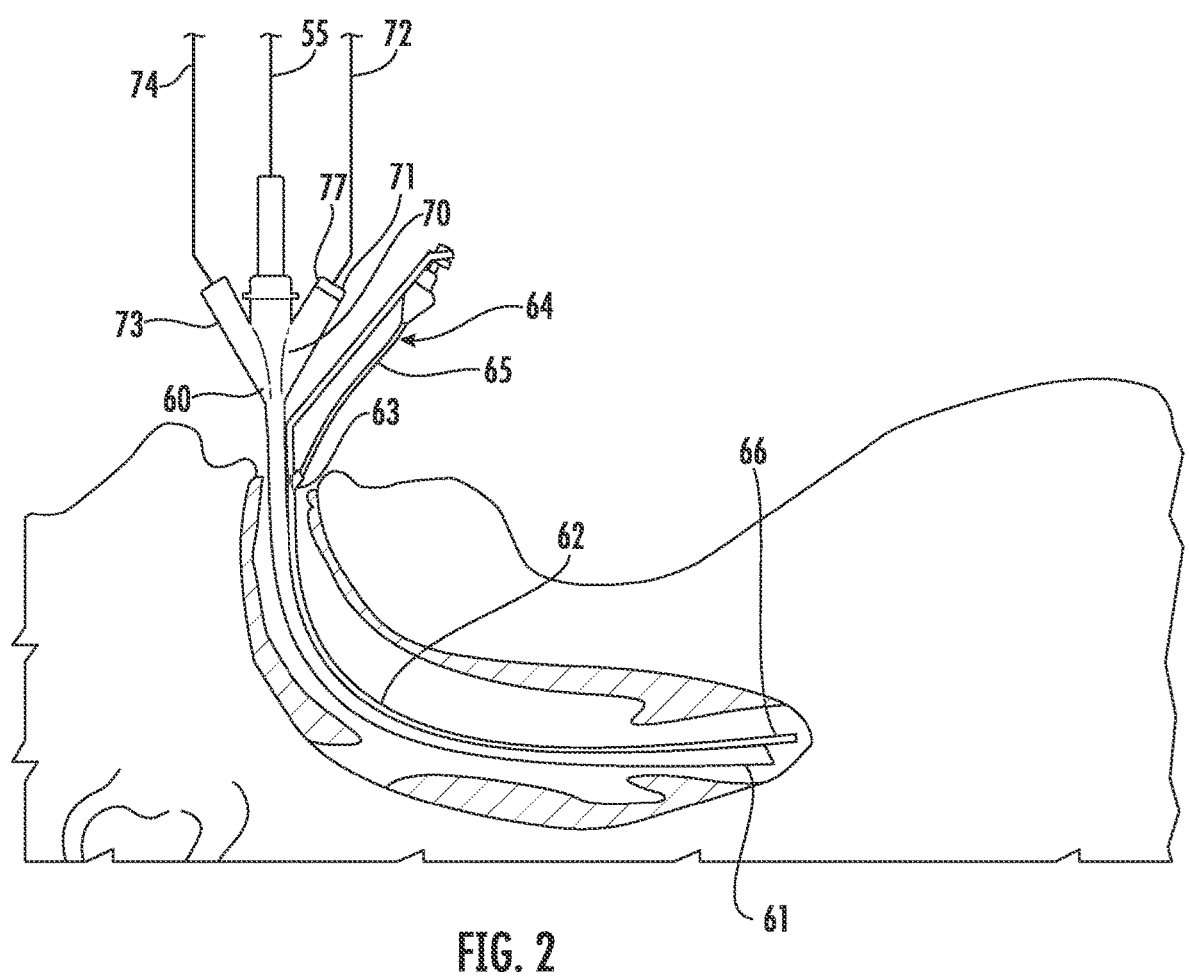
FIG. 2 is an enlarged view of the human patient applied with the liquid ventilation system.

The appliance 23 is shown in more detail in FIG. 2. It has at least three fittings at the upstream end 60. A first fitting is a port 70 that securely receives the injector 25 on the end of the administration line 55. The injector 25 is a fine-precision valve capable of receiving a high-pressure and/or high-volume fluid and dispensing it rapidly, in discrete volumes. Preferably, the injector 25 is a solenoid-controlled pintle valve injector capable of administering at least approximately five liters per minute. In a solenoid-controlled pintle valve injector, the pintle valve employs a needle which acts as a plunger within the solenoid, rapidly moving to open and close the valve in quick response to electronic control signals delivered to the solenoid. The injector 25 is coupled in electronic communication with the computer 67. Instructions from the computer 67 control and throttle the operation of the injector 25 in response to, at least, the intra-lung pressure measured by the sensor 64.

The port 70 is in open fluid communication with the cannula 62 such that fluid 21 supplied to the injector 25 is then dispensed by the injector 25 through the cannula 62 and out the downstream end 61 of the cannula 62, into the lungs of the patient 11. Because the injector 25 acts as a valve, the port 70 is essentially a one-way valve, only admitting downstream fluid 21 supplied from the tank 20.

A second fitting is a port 71 that securely receives an extraction line 72 of the system 10. The port 71 is in open fluid communication with the cannula 62 such that fluid 21 exiting the lungs of the patient 10 exits the appliance 23 through the port 71 and is then directed into the extraction line 72. The extraction line 72 extends back to the tank 20, as described later in this specification. Preferably, the port 71 includes a valve or a mechanical vacuum break 77, which prevents backflow of extracted fluid in the extraction line 72 to the appliance 23 and patient 11. The vacuum break 77 also prevents application of too much suction on the lungs, which could damage the lungs.

A third fitting is a port 73 which in some embodiments is closed and not used. In other embodiments, the port 73 is open and is connected to an oxygen line 74. The opposite end of the oxygen line 74 is connected to an oxygen supply 75 and a pump 76. The pump 76 is preferably, but not necessarily, carried within the housing 12 and pumps oxygen from the oxygen supply 75 into the oxygen line 74 for delivery to the appliance 23 and thus administration to the patient 11. In other embodiments, the oxygen pump 76 is actually a fast-acting valve. For example, where the oxygen supply 75 is "pure" oxygen delivered rapidly from a pressurized bottle, the fast-acting valve quickly toggles between open and closed positions to admit discrete, measured amounts of oxygen to the oxygen line 74.

The oxygen supply 75 may be internal to the housing 12, such as a canister of oxygen carried within the housing 12. In other embodiments, the oxygen supply 75 is external to the housing 12; a fitting or coupling on the outside of the housing 12 allows an oxygen supply 75 to be coupled to the pump 76 and oxygen line 74, used, and then disconnected or replaced. In other embodiments, the oxygen supply 75 is simply a filtered inlet from the atmosphere that admits atmospheric air. The oxygen provided through the oxygen line 74 is preferably administered to the patient in addition to the PFC fluids 21 supplied through the administration line 55.

The extraction line 72 returns exhaled fluid 21 to the tank 20. The extraction line 72 extends from the port 71 and includes an in-line filter 80 and a three-way extraction valve 81 downstream from the filter 80. Like the filter 41, the filter 80 separates particles, contaminants, and other elements from the exhaled fluid 21 before those exhaled fluids reach the tank 20. In the embodiment shown in FIG. 1, the extraction valve 81 is downstream from the filter 80 on the extraction line 72; in other embodiments, that arrangement is reversed.

The extraction valve 81 includes an upstream inlet 82, to which the extraction line 72 is coupled, a downstream outlet 83, to which another end of the extraction line 72 is coupled, and an exhaust outlet 84. An exhaust line 85 is coupled to the exhaust outlet 84 and extends to either an external exhaust or an environmental exhaust. In some embodiments, the exhaust line 85 is coupled to an environmental exhaust, which is a vent on the housing 12 that exhausts fluid or gas to the environment. In other embodiments, the exhaust line 85 is coupled to an external exhaust, such as a durable balloon or other expansion chamber coupled to the housing 12 at the exhaust line 85. The exhaust line 85 prevents over-pressurization of the system 10 and therefore protects the lungs.

From the downstream outlet 83, the extraction line 72 extends to and is coupled to the inlet 30 of the tank 20. In some embodiments, such as in FIG. 1, the extraction line 72 and the recirculation line 54 join upstream from the inlet 30, such as at a wye coupling.

In some embodiments, the system 10 additionally includes a carbon dioxide sensor 90 to perform capnography analysis by measuring the concentration or partial pressure of carbon dioxide exhaled through the extraction line 72. This analysis is a proxy for determining the proper placement of the appliance 23 within the patient 11, the effectiveness of chest compressions, the application of oxygen to the patient 11, and generally the effectiveness and functionality of the system 10 and PFC oxygenation. The carbon dioxide sensor 90 is preferably placed on an outlet of the suction pump 33 and is connected in data communication to the computer 67.

In operation, the computer 67 monitors readings from within the lungs of the patient 11, pressure and temperature values of the fluid 21 throughout the system 10, and the conditions within the tank 20 to rapidly administer PFC fluid 20 in coordination with the thumper 24 to cool the patient 11 efficiently.

When the patient 11 has suffered a traumatic event and is in a supine position, the appliance 23 is introduced to the patient 11. The patient 11 is unconscious for this procedure and may have no heartbeat. The downstream end 61 of the appliance 23 is passed through the oral cavity of the patient, past the esophagus and down the trachea. When the appliance 23 is properly located, the appliance 23 is connected to the lines 55, 72, and 74, if not already connected. If the sensor 64 is also not already applied to the appliance 23, it is threaded through the cannula 62 and located so that the transducer 66 is disposed just beyond the downstream end 61 of the appliance 23.

The appliance 23 is then fixed to the patient 11. Endotracheal tubes are often secured to the patient 11 with an armature supported by two adhesive pads on either side of the mouth. While such devices are suitable for fixing endotracheal tubes, they do not provide a seal around the oral cavity. As such, a balloon may be placed within the oral cavity and inflated to both hold the appliance 23 in place and to seal the oral cavity and thereby prevent exhalation and loss of pressure through the mouth. In other embodiments, there is also a device between the upstream and downstream ends of the appliance 23 which expands to form an impermeable seal between the cannula 62 and the inside of the trachea.

Figure 3:
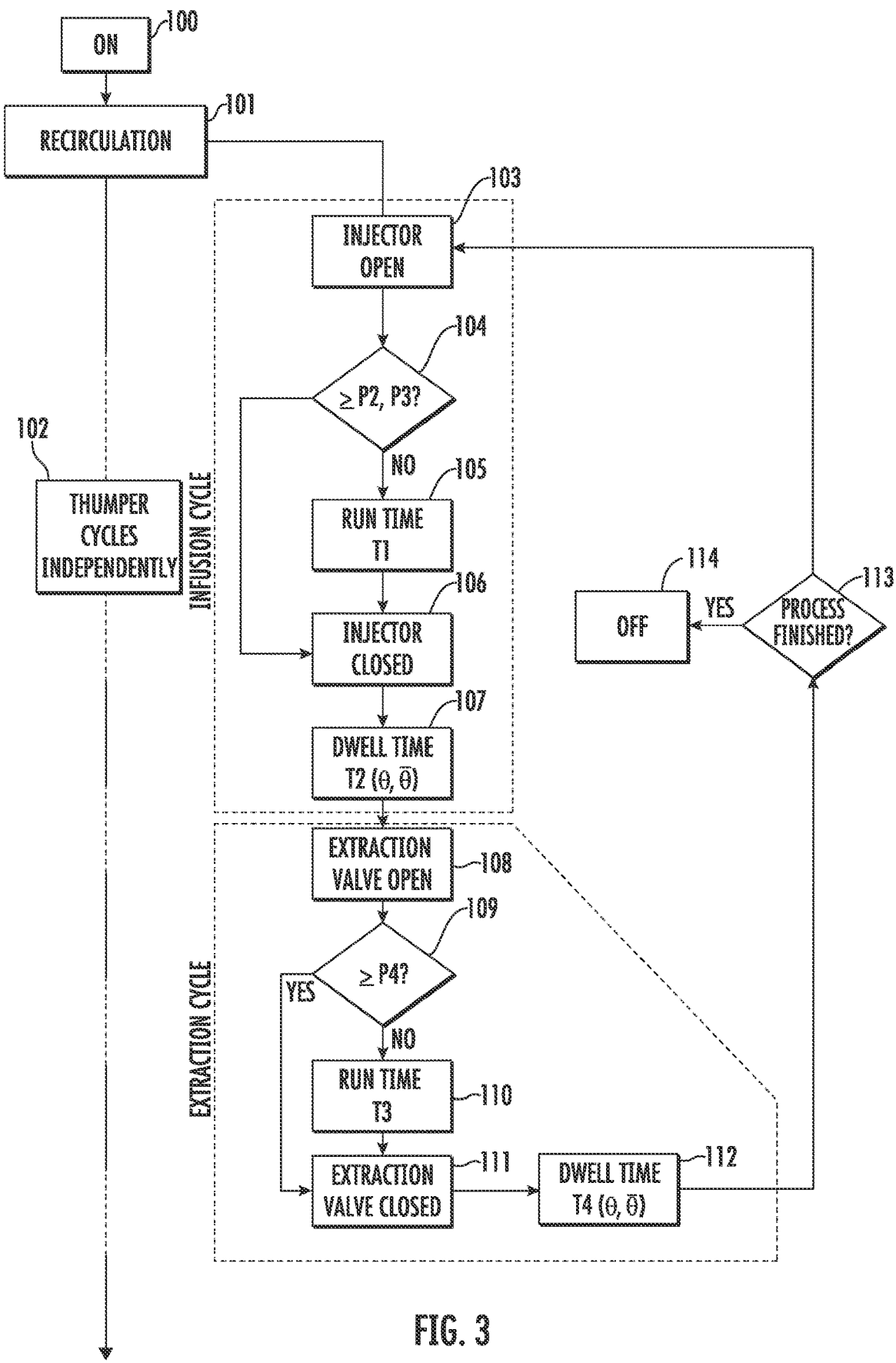
FIG. 3 is a timing chart illustrating operation of elements of the liquid ventilation system.

Once the patient 11 is prepared, the operator energizes the system 10, as time step 100 in FIG. 3. The chiller 22 preferably has already been filled with ice water or other cold media. The main pump 40 and suction pump 33 both activate. Fluid 21 within the tank 20 is pumped out of the tank 20, through the filter 41, and into the chiller 22 where heat exchange lowers the temperature of the fluid 21. The chilled fluid 21 moves through the chilled line 50 and past the thermocouple 56. The thermocouple 56 measures the temperature and sends the temperature measurement to the computer 67. The computer 67 is pre-programmed with instructions based in part on pre-determined thresholds for pressures and temperatures throughout the system 10. If the computer 67 determines that the fluid 21 in the chilled line 50 is not sufficiently cool to be administered to the patient 11, the computer 67 sends a control signal to the pressure regulator 51, instructing the regulator 51 to close the administration outlet 53 and open the recirculation outlet 52. Fluid 21 thus flows through the recirculation line 54 and then back to the tank 20. According to step 101, fluid 21 is recirculated until the computer 67 determines that the fluid 21 is sufficiently cool for administration to the patient 11. The pump 40 preferably operates in a low-speed setting during recirculation, but then operates at high speed during infusion of fluid 21 to the patient 11. The computer 67 also monitors the temperature in the tank 20 itself, according to the readings from the thermocouple 36 therein.

Meanwhile, at step 102, the thumper 24 performs CPS on the chest of the patient 11 to circulate blood throughout the patient 11. The thumper 24 operates rapidly, with stroke cycles of approximately one-hundredth of a minute, or one hundred strokes per minute (other frequencies are suitable). In most embodiments, the thumper 24 operates independently of the infusion and extraction of fluid 21 to the patient. FIG. 3 illustrates the independent, cyclic action of the thumper 21 and the controlled, responsive action of the injector 25 and extraction valve 81.

The injector 25 and extraction valve 81 control the infusion and extraction cycles. These happen over periods of time during which one or several thumper 24 strokes may occur. While the infusion and extraction cycles are responsive to the state of the system 10 and the thumper 24 is part of that system 10, the infusion and extraction cycles are not necessarily directly dependent on the state of the thumper 24. Rather, certain measurements and thresholds, preset into the system 10 or dynamically generated by the computer 67, govern control of the system 100.

Infusion begins once the fluid 21 has reached a suitable temperature, or when the operator initiates administration by actuating a button, switch, or user interface element. Infusion begins at step 103, with the injector 25 opening. Throughout operation, the pressure regulator 51 maintains a pre-determined pressure level inside the administration line 55 so that when the injector 25 opens and releases fluid to the patient 11, the pressure in the administration line 55 remains constant despite the release of fluid through the injector 25. The injector 25 is at the end of the administration line 55, mounted in the upstream end 60 of the appliance 23. Now, rather than being recirculated, most if not all of the fluid 21 is supplied toward the patient 11 through the administration line 55 and the injector 25. The system 100 will continuously attempt to introduce more PFC fluid 21 into the patient 11 by maintaining pressure in the administration line 55. Some fluid 21 will continue to be circulated, but only that amount which is in excess of the lung capacity of the patient 10. The infusion cycle continues unless one of two triggering events occurs.

Occurrence of a pressure spike or a maximum pressure triggers the infusion cycle to stop. The computer 67 is connected in data communication to the intra-lung transducer 66 and monitors information therefrom, including pressure signals from the transducer 67 which allow the computer 67 to determine the cycle position of the thumper 24. In some embodiments, the computer 67 is also connected in data communication to the thumper 24 and monitors information from it. The computer 67 monitors the pressure inside the lungs and controls infusion accordingly.

If the intra-lung pressure reaches a maximum pressure value P2 for a non-transient duration of time (as indicated at step 104), then the computer 67 will instruct the injector 25 to close (step 106). This indicates that the lungs are essentially full and cannot accept any further fluid 21. The computer 67 will also instruct the injector 25 to close if the intra-lung pressure reaches a maximum pressure value P3 for a transient duration of time, such as a pressure spike at P3. This indicates that the lungs are at least partially filled with fluid 21 and that the thumper 24 is at least partially compressing the chest, reducing the lung volume, and therefore increasing the intra-lung pressure. Under both of these scenarios, closing the injector 25 prevents administration of further fluid 21 and prevents the intra-lung pressure from rising further, thereby protecting the lungs from damage.

If neither triggering event occurs, then the infusion cycle continues for a run time Tl, as indicated at step 105. The length of run time T1 is preset but may be dynamically changed by the computer 67 during operation of the system 100 based on system characteristics. After the run time T1 has elapsed since infusion began, the injector 25 closes (step 106). The infusion cycle ends after a dwell time T2 (step 107). The dwell time T2 is typically short, and in some cases is zero.

After the infusion cycle, the extraction cycle begins with the extraction valve 81 opening at step 108.

During the extraction cycle, the computer 67 actuates the downstream three-way extraction valve 81 to open the extraction line 72 between the higher-pressure lungs and the lower-pressure tank 20. This causes the fluid 21 to be exhausted and energetically extracted from the lungs to the tank 20. The suction pump 33 runs continuously, drawing fluid 21 out of the patient 11 through the extraction line 72. When the extraction valve 81 is opened and fluid 21 is quickly drawn through the extraction line 81, this lowers the vacuum level (raises the pressure) in the tank 20 but does not completely deplete the vacuum.

The extraction valve 81 remains open unless a triggering event occurs. If the computer 67 detects that the intra-lung pressure experiences a negative spike (step 109), or a transient reduction in pressure below a minimum pressure value P4, then the computer 67 instructs the extraction valve 81 to close (step 111).

If the intra-lung sensor does not record a negative pressure spike, then the extraction cycle continues for a run time T3, as indicated in step 110. The length of the run time T3 is preset but may be dynamically changed by the computer 67 during operation of the system 100 based on system characteristics. After the run time T3 has elapsed since the extraction began, the extraction valve 81 closes (step 111). The extraction cycle then ends after a dwell time T4 (step 112), which is typically short and in some cases is zero. The swell time T4 allows the suction pump 33 to draw down the vacuum level in the tank 20 in preparation for the next infusion cycle.

In some portions of either the infusion or extraction cycle, the exhaust outlet 84 on the extraction valve 81 is opened. Opening the exhaust outlet 84 of the valve 81 creates a more natural open pathway from the lungs to either the environment or to an expansion chamber, thereby preventing damage to the lungs.

At step 113, the process either finishes or returns to step 103 for another infusion and extraction cycle. If the process finishes, the system turns off at step 114. If not, then the process of infusion and extraction repeats until the patient 11 is cooled sufficient and the process may then be finished.

As noted above, the transducer 66 preferably measures both intra-lung pressure and temperature, and there is preferably a backup sensor. In the event that both the transducer 66 and the backup sensor fail, however, the system 10 is capable of reverting to administering fluid 21 based on the operation of the thumper 24. In such an event, the computer 67 controls activation of the injector 25 in response to the movement of the thumper 24. Because the pressure regulator 51 maintains pressure to the injector 25 at a known level, and because the computer 67 knows the performance characteristics of the injector 25, the computer 67 determines a highly-accurate estimate the volume of fluid 21 applied by the injector 25 during each administration cycle. Therefore, in the unlikely event that the computer 67 is unable to measure the intra-lung pressure, it continues to operate the system 10 to safely administer fluid 21 to the patient 11.

In embodiments of the system 10 which do not employ a thumper 24, the transducer 66 monitors the intra-lung pressure, and the computer 67 allows full administration of the PFC fluid 21 to the patient 11 until the predetermined maximum intra-lung pressure is detected.

Fluid 21 extracted from the patient 11 leaves the patient 11 through the extraction line 72. While in the patient 11, the fluid 21 may be mixed with gas, such as atmospheric air, oxygen, carbon dioxide, or other gasses from the natural exchange that occurs in lungs during breathing. These gasses are bubbles in the fluid 21, and the bubbles travel with the fluid 21 back to the tank 20. However, once returned to the tank 20, the suction pump 33 removes these bubbles. The suction pump 33 draws the bubbles out of the fluid 21 before the fluid 21 is supplied to the chiller 22. This prevents introduction of fluid 21 carrying gas bubbles to the pump 40, which could possibly cavitate. Gas bubbles suctioned from the tank 20 are exhausted through the outlet 35 of the pump 33.

In embodiments of the system 10 which include the oxygen supply 75, the computer 67 controls the pump 76 and thus controls administration of supplemental or atmospheric oxygen to the patient through the appliance 23. Embodiments of the system that include the carbon dioxide sensor 90 are especially suitable for controlling administration of oxygen, as the capnography analysis the computer 67 performs based on the readings from the carbon dioxide sensor 90 informs whether the patient 11 is receiving an acceptable supply of oxygen.

A preferred embodiment is fully and clearly described above so as to enable one having skill in the art to understand, make, and use the same. Those skilled in the art will recognize that modifications may be made to the description above without departing from the spirit of the specification, and that some embodiments include only those elements and features described, or a subset thereof. To the extent that modifications do not depart from the spirit of the specification, they are intended to be included within the scope thereof.

What is claimed is:

1. A liquid ventilation system comprising:
a reservoir holding a perfluorochemical (PFC) fluid, and a heat exchanger downstream from the reservoir;
an appliance configured to be disposed within a patient, the appliance coupled in fluid communication downstream from the reservoir;
a sensor in the appliance configured to measure an intra-lung pressure;
an injector configured to supply the PFC fluid through the appliance in response to measurements of the intra-lung pressure from the sensor;
a pressure regulator configured to maintain a pressure of the fluid at the injector;
an exchanger-regulator line from the heat exchanger to the pressure regulator;
an administration line from the pressure regulator to the injector;
a recirculation line from the pressure regulator to the reservoir; and
the pressure regulator is arrangeable between a first position enabling fluid communication from the heat exchanger to the injector and disabling fluid communication from the heat exchanger to the reservoir and a second position enabling fluid communication from the heat exchanger to the reservoir and disabling fluid communication from the heat exchanger to the injector.

2. The liquid ventilation system of claim 1, further comprising a suction pump connected to the reservoir to reduce pressure within the reservoir.

3. The liquid ventilation system of claim 1, further comprising an extraction valve disposed on an extraction line between the appliance and the reservoir, the extraction valve arrangeable between a first position enabling fluid communication from the appliance to the reservoir and a second position disabling fluid communication from the appliance to the reservoir.

4. The liquid ventilation system of claim 3, wherein the second position of the extraction valve enables fluid communication from the appliance to an exhaust.

5. The liquid ventilation system of claim 1, wherein the injector is configured to supply the PFC fluid in response to measurements of the intra-lung pressure from the sensor.

6. A liquid ventilation system comprising:
a reservoir holding a perfluorochemical (PFC) fluid, a suction pump connected to the reservoir to reduce pressure within the reservoir, and a heat exchanger downstream from the reservoir;
a sensor configured to measure an intra-lung pressure;
an appliance configured to be disposed within a patient, the appliance carrying an injector to supply the PFC fluid through the appliance;
a pressure regulator configured to maintain a pressure of the fluid at the injector;
an extraction valve disposed on an extraction line between the appliance and the reservoir, the extraction valve arrangeable between a first position enabling fluid communication from the appliance to the reservoir and a second position disabling fluid communication from the appliance to the reservoir;
an exchanger-regulator line from the heat exchanger to the pressure regulator;
an administration line from the pressure regulator to the injector;
a recirculation line from the pressure regulator to the reservoir; and
the pressure regulator is arrangeable between a first position enabling fluid communication from the heat exchanger to the injector and disabling fluid communication from the heat exchanger to the reservoir and a second position enabling fluid communication from the eat exchanger to the reservoir along the recirculation line and disabling fluid communication from the heat exchanger to the injector.

7. The liquid ventilation system of claim 6, wherein, when the extraction valve is in the first position thereof, the suction pump is configured to operate to extract PFC fluid from the appliance into the reservoir.

8. The liquid ventilation system of claim 6, wherein the injector is configured to supply the PFC fluid in response to measurements of the intra-lung pressure from the sensor.

9. The liquid ventilation system of claim 6, wherein the second position of the extraction valve enables fluid communication from the appliance to an exhaust.

10. A liquid ventilation system comprising:
a reservoir holding a perfluorochemical (PFC) fluid, a suction pump connected to the reservoir to reduce pressure within the reservoir, and a heat exchanger downstream from the reservoir;
an appliance configured to be disposed within a patient, the appliance carrying an injector to supply the PFC fluid to the patient;
a pressure regulator configured to maintain pressure of the fluid at the injector;
an extraction valve disposed on an extraction line between the appliance and the reservoir, the extraction valve arrangeable between a first position enabling fluid communication from the appliance to the reservoir and a second position disabling fluid communication from the appliance to the reservoir;
an exchanger-regulator line from the heat exchanger to the pressure regulator;
an administration line from the pressure regulator to the injector;
a recirculation line from the pressure regulator to the reservoir; and
the pressure regulator is arrangeable between a first position enabling fluid communication from the heat exchanger to the injector and disabling fluid communication from the heat exchanger to the reservoir and a second position enabling fluid communication from the heat exchanger to the reservoir along the recirculation line and disabling fluid communication from the heat exchanger to the injector.

11. The liquid ventilation system of claim 10, wherein the second position of the extraction valve enables fluid communication from the appliance to an exhaust.

12. The liquid ventilation system of claim 10, further comprising a sensor in the appliance configured to measure an intra-lung pressure of the patient, wherein the injector supplies the PFC fluid in response to measurements of the intra-lung pressure from the sensor.

* * * * *